US011305157B2

(12) United States Patent
Yu et al.

(10) Patent No.: US 11,305,157 B2
(45) Date of Patent: Apr. 19, 2022

(54) WEIGHT TRAINING METHOD, APPARATUS AND SYSTEM

(71) Applicant: Industrial Technology Research Institute, Hsinchu (TW)

(72) Inventors: Tzu-Hao Yu, Yilan County (TW); Tzu-Yang Ting, Taipei (TW); Yun-Yi Huang, Pingtung County (TW); Chien-Hsun Chu, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 282 days.

(21) Appl. No.: 16/745,369

(22) Filed: Jan. 17, 2020

(65) Prior Publication Data

US 2021/0023416 A1 Jan. 28, 2021

(30) Foreign Application Priority Data

Jul. 22, 2019 (TW) .................................. 108125787

(51) Int. Cl.
*A63B 24/00* (2006.01)
*A61B 5/11* (2006.01)

(52) U.S. Cl.
CPC ........ *A63B 24/0006* (2013.01); *A61B 5/1107* (2013.01); *A61B 5/1126* (2013.01); (Continued)

(58) Field of Classification Search
CPC ............ A63B 24/0006; A63B 24/0062; A63B 24/0075; A63B 2024/0009; (Continued)

(56) References Cited

U.S. PATENT DOCUMENTS

2014/0135174 A1* 5/2014 Potash ............... A63B 23/0494
482/8
2014/0200432 A1* 7/2014 Banerji .............. A63B 21/4017
600/383
(Continued)

FOREIGN PATENT DOCUMENTS

CN 101513567 8/2009
CN 202087001 12/2011
(Continued)

OTHER PUBLICATIONS

"Office Action of Taiwan Counterpart Application", dated Aug. 21, 2020, p. 1-p. 4.
(Continued)

*Primary Examiner* — Sundhara M Ganesan
(74) *Attorney, Agent, or Firm* — JCIPRNET

(57) ABSTRACT

A weight training method, a weight training apparatus and a weight training system are provided. In the method, a weight of a load of a user operating the weight training apparatus is detected by a load sensor, a motion of the load is detected by an activity sensor, and thereby an operation power of the weight training apparatus is calculated. A force applied by the muscle portion when the user operates the weight training apparatus is detected by at least one biophysical quantity sensor disposed on at least one muscle portion of the user and used to calculate an energy power consumed by the user. An exercise efficiency value of the user is calculated by using the energy power and the operation power, and the user is prompted to adjust an operation performed on the weight training apparatus when the exercise efficiency value drops beyond a preset ratio.

15 Claims, 6 Drawing Sheets

(52) U.S. Cl.
CPC ...... *A63B 24/0062* (2013.01); *A63B 24/0075* (2013.01); *A63B 2024/0009* (2013.01); *A63B 2024/0065* (2013.01); *A63B 2024/0078* (2013.01); *A63B 2220/51* (2013.01); *A63B 2220/836* (2013.01); *A63B 2230/085* (2013.01)

(58) Field of Classification Search
CPC .... A63B 2024/0065; A63B 2024/0078; A63B 2220/51; A63B 2220/836; A63B 2230/085; A63B 71/0619; A63B 21/06; A63B 2220/80; A61B 5/1107; A61B 5/1126; A61B 5/1118; A61B 5/486; A61B 5/6895; A61B 5/389; A61B 5/221
See application file for complete search history.

(56) References Cited

U.S. PATENT DOCUMENTS

| | | | | |
|---|---|---|---|---|
| 2016/0199245 | A1* | 7/2016 | Mikulski | A63B 24/0087 601/33 |
| 2017/0209737 | A1* | 7/2017 | Tadi | A61H 1/0281 |
| 2018/0178062 | A1* | 6/2018 | Chirosa Rios | A63B 22/00 |
| 2018/0264318 | A1* | 9/2018 | Fung | A63F 13/214 |
| 2019/0126090 | A1 | 5/2019 | O'Connor | |
| 2019/0314680 | A1* | 10/2019 | Hwang | A63B 71/0622 |
| 2020/0038703 | A1* | 2/2020 | Cleary | A61H 1/0266 |
| 2020/0330849 | A1* | 10/2020 | Bleich | A63B 24/0062 |
| 2021/0260444 | A1* | 8/2021 | Huang | A63B 24/0062 |

FOREIGN PATENT DOCUMENTS

| | | |
|---|---|---|
| CN | 105597298 | 5/2016 |
| CN | 106110630 | 11/2016 |
| CN | 109621329 | 4/2019 |
| CN | 109865247 | 6/2019 |
| EP | 2586502 | 5/2013 |
| TW | 200916146 | 4/2009 |
| TW | M397839 | 2/2011 |
| TW | M518095 | 3/2016 |
| TW | I559905 | 12/2016 |
| TW | 201722352 | 7/2017 |

OTHER PUBLICATIONS

Sun Ming-Yun et al., "Work efficiency during movement: Detection using energy and biomechanical methods," Chinese Journal of Tissue Engineering Research, vol. 17, No. 11, Mar. 12, 2013, pp. 2032-2039.

"Office Action of China Counterpart Application", dated May 19, 2021, p. 1-p. 8.

* cited by examiner

WEIGHT TRAINING METHOD, APPARATUS AND SYSTEM

CROSS-REFERENCE TO RELATED APPLICATION

This application claims the priority benefit of Taiwan application no. 108125787, filed on Jul. 22, 2019. The entirety of the above-mentioned patent application is hereby incorporated by reference herein and made a part of this specification.

TECHNICAL FIELD

The disclosure relates to a fitness method and a fitness system, and also relates to a weight training method, a weight training apparatus and a weight training system.

BACKGROUND

With the number of fitness centers increased year by year due to the awareness of physical exercise today, weight training is one of fitness exercises that people often choose. At present, in the weight training, people have no other way to know whether they have inappropriate postures or inappropriate operations on equipments during the weight training, except through on-site coaching.

However, inappropriate postures or inappropriate operations on equipments often lead to uncoordinated movements of the limbs, resulting in sports injuries such as strains, contusions, etc. In addition, an excessive exercise time may cause muscle overwork and increase the possibility of sports injuries. If the exercise time is too short, an ideal effect from the weight training may not be achieved.

SUMMARY

An embodiment of the disclosure provides a weight training method, which is adapted to a weight training system including a computing device, a load sensor, an activity sensor and at least one biophysical quantity sensor. The biophysical quantity sensor is disposed on at least one muscle portion of a user. In the method, a weight of a load of the user operating the weight training apparatus is detected by the load sensor, a motion of the load is detected by the activity sensor, and thereby an operation power of the weight training apparatus is calculated. A force applied by the at least one muscle portion when the user operates the weight training apparatus is detected by the biophysical quantity sensor, and thereby an energy power consumed by the user is calculated. An exercise efficiency value of the user is calculated by using the energy power and the operation power, and the user is prompted to adjust an operation performed on the weight training apparatus when the exercise efficiency value drops beyond a preset ratio.

An embodiment of the disclosure provides a weight training system, which includes a load sensor, an activity sensor, at least one biophysical quantity sensor and a computing device. The load sensor is configured to detect a weight of a load of a weight training apparatus. The activity sensor is configured to detect a motion of the load. The biophysical quantity sensor is disposed on at least one muscle portion of the user, and configured to detect a force applied by the at least one muscle portion when the user operates the weight training apparatus. The computing device is coupled to the load sensor, the activity sensor and the biophysical quantity sensor, and configured for calculating an operation power of the weight training apparatus by using the detected weight and the detected motion of the load; using the detected force applied by the at least one muscle portion to calculate an energy power consumed by the user; and calculating an exercise efficiency value of the user by using the energy power and the operation power, and prompting the user to adjust an operation performed on the weight training apparatus when the exercise efficiency value drops beyond a preset ratio.

An embodiment of the disclosure provides a weight training system, which includes a computing device, a load sensor, an activity sensor and at least one biophysical quantity sensor. The load sensor is configured to detect a weight of a load of a weight training apparatus. The activity sensor is configured to detect a motion of the load. The biophysical quantity sensor is disposed on at least one muscle portion of the user, and configured to detect a force applied by the at least one muscle portion when the user operates the weight training apparatus. The computing device is coupled to the load sensor, the activity sensor and the biophysical quantity sensor, and configured for calculating an operation power of the weight training apparatus by using the detected weight of the load and the detected motion of the load; using the detected force applied by the at least one muscle portion to calculate an energy power consumed by the user; and calculating an exercise efficiency value of the user by using the energy power and the operation power. The weight training apparatus is determined as being encountering an abnormality when the exercise efficiency value is greater than 1, and a provider of the weight training apparatus is prompted to eliminate the abnormality. The operation of the user is determined as being inappropriate when the exercise efficiency value is less than 1, and the user is prompted to adjust the operation.

To make the disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION

Figure 1:
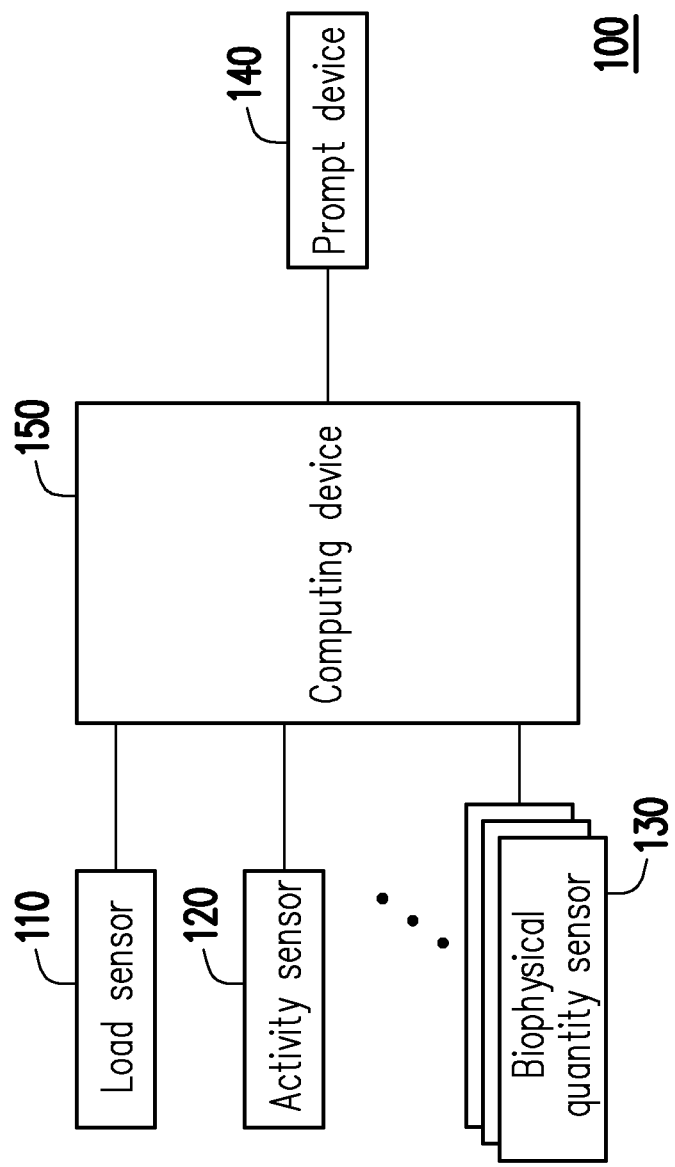
FIG. 1 illustrates a block diagram of the weight training system according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The embodiments of the disclosure provide a weight training system that integrates a device operation power detection with a human body consumed energy detection, which is capable of using a sensor disposed on a weight training apparatus to calculate a device operation power by detecting a weight and a motion of a load, and using a biophysical quantity sensor disposed on a muscle portion that applies a force to calculate an energy power consumed by the human body by detecting the applied force. By analyzing changes between the energy power consumed by the human body and the device operation power according to the embodiment of the disclosure, whether inappropriate postures or inappropriate operations of the equipment occur during a process of the weight training for the human body can be determined, and an instant visual or auditory feedback can be provided when inappropriate postures or inappropriate operations are found. In this way, the user can improve the weight training effect and avoid sports injuries.

FIG. 1 illustrates a block diagram of the weight training system according to an embodiment of the disclosure. With reference to FIG. 1, a weight training system 100 of this embodiment includes a load sensor 110, an activity sensor 120, at least one biophysical quantity sensor 130, a prompt device 140 and a computing device 150.

The load sensor 110 is, for example, a plug sensor disposed on a load plug of a weight training apparatus (not shown). When the plug is inserted to a bumper plate, the load sensor 110 can read an RFID tag of the inserted bumper plate through an RFID (Radio Frequency Identification) reader, and detect a weight of a load selected by a user. In other embodiments, the load sensor 110 may also be any sensors capable of detecting the weight of the load such as an infrared sensor, a Hall sensor and the like, and this embodiment is not limited thereto.

The activity sensor 120 includes one or more of the following: a GPS (global positioning system) sensor, an accelerometer, a directional sensor, an electronic compass, a gyroscope sensor, a timer sensor and a motion sensor, which are, for example, disposed on the load of the weight training apparatus and configured to detect a motion of the weight. When the load moves along with a force applied by the user, the activity sensor 120 can detect a three-dimensional acceleration of the load, and can calculate a velocity of the load by performing an integral operation on the detected acceleration.

The biophysical quantity sensor 130 intercepts biological motion information through a bioelectrical detection, a biomagnetic detection or a non-electromagnetic physiological parameter detection. The biophysical quantity sensor 130 may be a neuromuscular sensor, including: an EMG sensor (Electromyography sensor), an MMG sensor (Mechanomyography sensor), and a SMG sensor (Sonomyography sensor). The biophysical quantity sensor 130 may be implemented by, for example, clothing (e.g., jackets, tops, pants, skirts, underclothes, etc.), accessory (e.g., gloves, bracelets, ankle rings, hats, socks, belts, headscarves, cufflinks, etc.), patches, straps, waist protectors, knee protectors, ankle protectors or shoes that can be worn by the user, but not limited thereto. The biophysical quantity sensor 130 is disposed on, for example, at least one muscle portion of the user that applies the force during the weight training. For example, when the user performs a sitting rowing in the weight training, the biophysical quantity sensor 130 may be respectively disposed on biceps brachii and latissimus dorsi of the user to detect the applied force; when the user performs a zip line vertical rowing in the weight training, the biophysical quantity sensor 130 may be respectively disposed on deltoid and trapezius of the user to detect the applied force.

The prompt device 140 is, for example, a display, a speaker, a light-emitting diode (LED) array or a vibrator or any combination of the above. The prompt device 140 can accept the control of the computing device 150, warn the user about inappropriately applied forces or inappropriate operations in various (visual, audible, and/or tactile) ways, and prompt the user to correct the current actions or postures.

The load sensor 110, the activity sensor 120, the biophysical quantity sensor 130 and the prompt device 140 are respectively connected to the computing device 150 in a wired or wireless manner via a connecting device (not shown). The wired connection device may be universal serial bus (USB), RS232, universal asynchronous receiver/transmitter (UART), inter-integrated circuit (I2C), serial peripheral interface (SPI), display port, thunderbolt or local area network (LAN) interfaces, but not limited thereto. The wireless connection device may be a device that supports communications protocols including Wi-Fi (wireless fidelity), RFID, Bluetooth, infrared, NFC (near-field communication) or D2D (device-to-device), but not limited thereto.

The computing device 150 includes, for example, a storage device and a processor (not illustrated). Here, the storage device is, for example, a random access memory (RAM), a read-only memory (ROM), a flash memory, a hard disk driver in any possible forms or other similar elements, or a combination of the above-mentioned elements. The processor is, for example, a central processing unit (CPU) or other programmable devices for general purpose or special purpose such as a microprocessor and a digital signal processor (DSP), a programmable controller, an application specific integrated circuit (ASIC) or other similar devices or a combination of above-mentioned devices. In this embodiment, the processor can load in a computer program from the storage device to execute the weight training method according to the embodiments of the disclosure.

In the foregoing embodiment, the computing device 150 of the weight training system 100 is set independently of the weight training apparatus. For example, the computing device 150 may be constructed, for example, on a computer or server of an operator (e.g., a gym operator), or may be constructed on a portable device owned by the user such as a mobile phone, so as to monitor the user during the process of the weight training and provide immediate operation prompts. However, in other embodiments, the weight training system 100 may also be integrated inside the weight training apparatus to allow the user who uses the apparatus to directly obtain, from the apparatus, all information required for operating the apparatus, and receive the operation prompt suitable for a current state from the apparatus during the process of the weight training.

Figure 2:
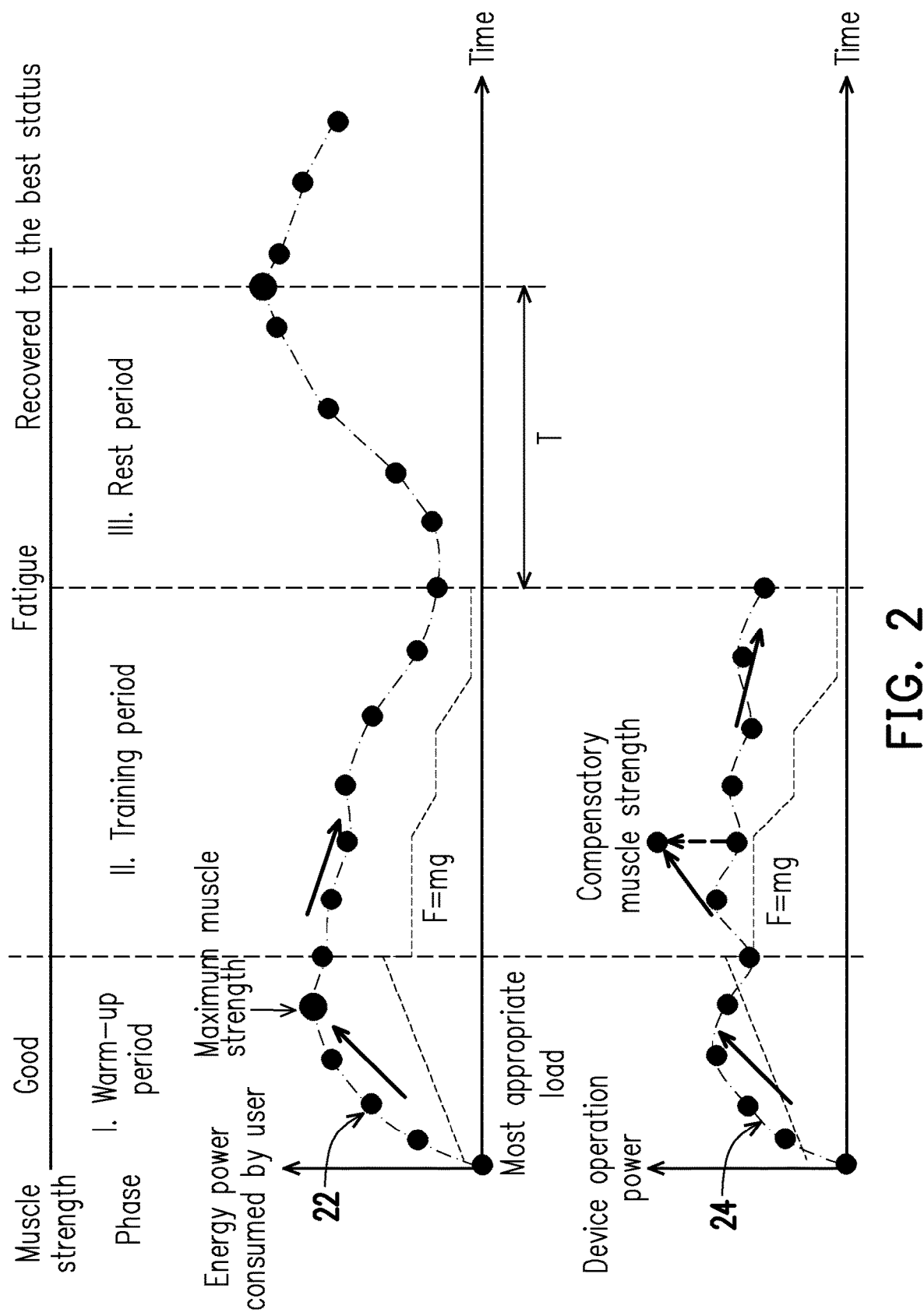
FIG. 2 illustrates a sensor measurement timing diagram in the weight training method according to an embodiment of the disclosure.

FIG. 2 illustrates a sensor measurement timing diagram in the weight training method according to an embodiment of the disclosure. With reference to FIG. 2, in this embodiment, the process of the weight training for the user using the weight training apparatus is divided into: I. a warm-up period, II. a training period, and III. a rest period. In the drawing, a curve "F=mg" is a weight of the bumper plate, with ups and downs representing that the user gradually increases or decreases the weight of the load as the training progresses. During each period, the biophysical quantity sensor disposed on the muscle portion of the user that applies the force is used to detect a magnitude of the force applied by the user, calculate an energy power consumed by the user at each time point, and generate an energy power (consumed by the user) chart 22. Meanwhile, the activity sensor disposed on the load of the weight training apparatus is also used to detect the motion of the load, calculate the operation power of the weight training apparatus at each time point together with the weight of the load, and generate a device operation power chart 24. Here, for each period, a peak vale in the curve of the energy power chart 22 may also be used to detect a maximum muscle strength of the user.

Comparing the energy power (consumed by the user) chart 22 with the device operation power chart 24, it can be seen that during the warm-up period, the energy power consumed by the user gradually increases. These changes are consistent with changes in the device operation power. During the training period, the energy power consumed by the user gradually decreases due to a muscle fatigue. These changes should be consistent with changes in the device operation power. However, if the device operation power increases but the energy power consumed by the user decreases at this time (which means that the user has changed to apply the force by using a compensatory muscle strength), continuance of this situation may lead to sports injuries. In this case, the user can be prompted to reduce the weight or correct the postures so as to avoid sports injuries. On the other hand, this embodiment can also calculate a ratio of the energy power consumed by the user and the device operation power as an exercise efficiency value of the user. Here, when the exercise efficiency value drops beyond a preset ratio (which means that the muscle strength of the user can no longer bear a burden of the current load), the user can be prompted to reduce the weight so as to improve the exercise efficiency value and avoid sports injuries.

Figure 3:
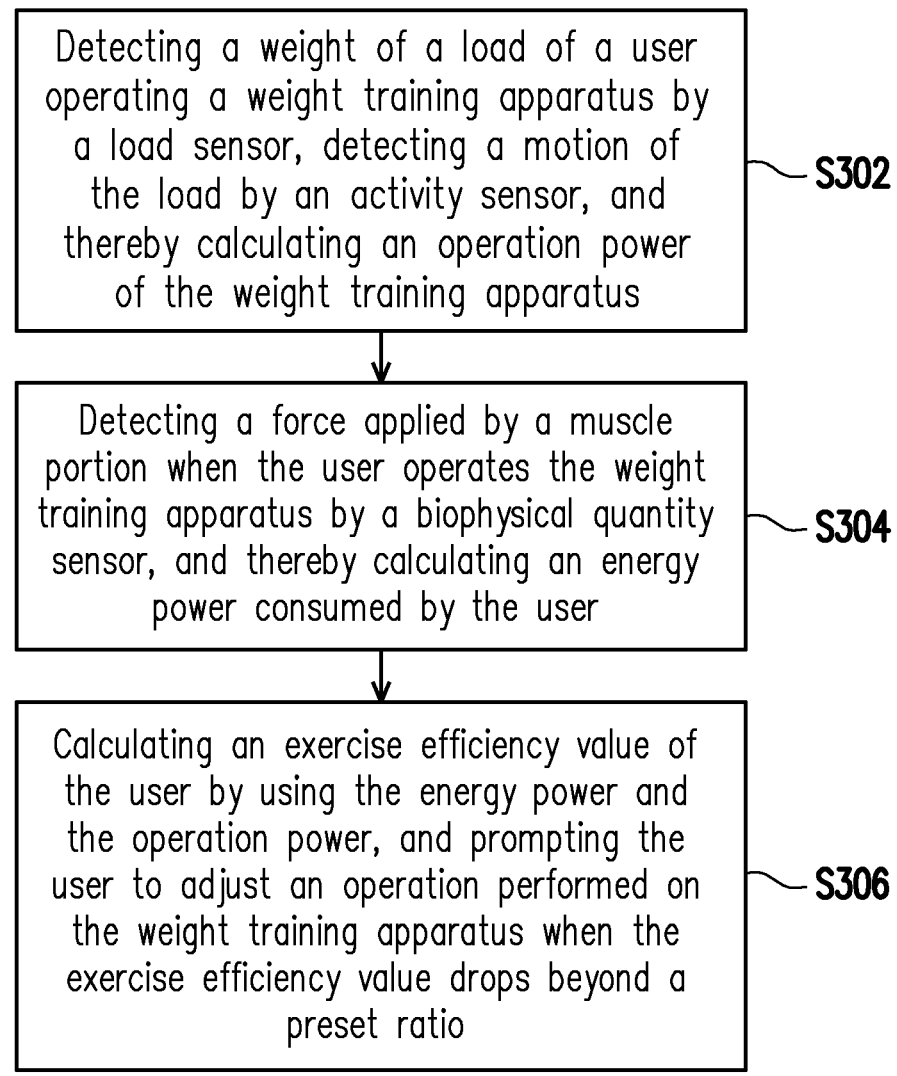
FIG. 3 illustrates a flowchart of the weight training method according to an embodiment of the disclosure.

FIG. 3 illustrates a flowchart of the weight training method according to an embodiment of the disclosure. Referring to FIG. 1 and FIG. 3 together, the method of this embodiment is adapted to the weight training system 100 of FIG. 1. Detailed steps in the weight training method according to the embodiments of the disclosure are described below with reference to interactions between various devices in the weight training system 100.

First, in step S302, the load sensor 150 detects a weight of a load of a user operating a weight training apparatus by the load sensor 110, detects a motion of the load by the activity sensor 120, and thereby calculates an operation power of the weight training apparatus. In an embodiment, when the user inserts the plug to the bumper plate of the load, the RFID reader disposed on the plug can read the RFID of the bumper plate and know the weight of the load selected by the user. On the other hand, the user may also place the patch or the device disposed with the gravity sensor on the load so that the gravity sensor can detect the three-dimensional acceleration ($a_x$, $a_y$, $a_z$) of the load to which the force is applied, and calculate a velocity V through the integral operation. The computing device 150 calculates an applied force F generated by the load by the formula of F=ma, and multiplies the calculated applied force F by the velocity V by the formula of P=FV to calculate an operation power P of the weight training apparatus.

Before the user starts the weight training, an embodiment of the disclosure further includes: displaying a prompt screen on the prompt device 140 by the computing device 150 to request the user to input basic physiological parameters such as height, weight, age and the like and to set a specific portion to be trained or the type of equipment to be used. Based on the settings of the user, the computing device 150 can prompt a training method of the equipment on the prompt device 140, instruct the user to place the patch or the strap disposed with the activity sensor 120 on a suitable position of the equipment (e.g., on the bumper plate), and fix the clothing, the accessory, the patch or the strap disposed with the biophysical quantity sensor 130 on a suitable muscle portion. Then, the computing device 150 can perform an orientation correction on the activity sensor 120 or perform a compensation correction on a position where the biophysical quantity sensor 130 is worn, so as to improve accuracy for the sensors.

In addition, after the user starts the weight training, an embodiment of the disclosure further includes: correcting operation actions or postures of the user by the computing device 150 before calculating the operation power.

The computing device 150 can detect an inclined angle of a handle of the weight training apparatus (e.g., disposed on the middle, two ends or other positions of the handle) when the user operates the weight training apparatus by at least one gravity sensor disposed on the handle, and determine whether the handle is skew according to the detected inclined angle to prompt the user to correct the operation.

Figure 4A:
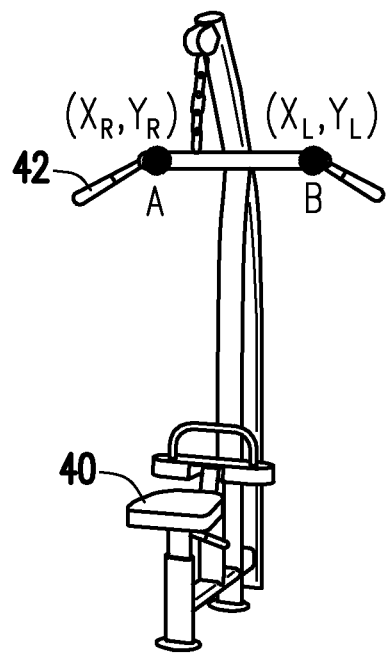
FIG. 4A and FIG. 4B are schematic diagrams illustrating actions for correcting the operation according to an embodiment of the disclosure.
Figure 4B:
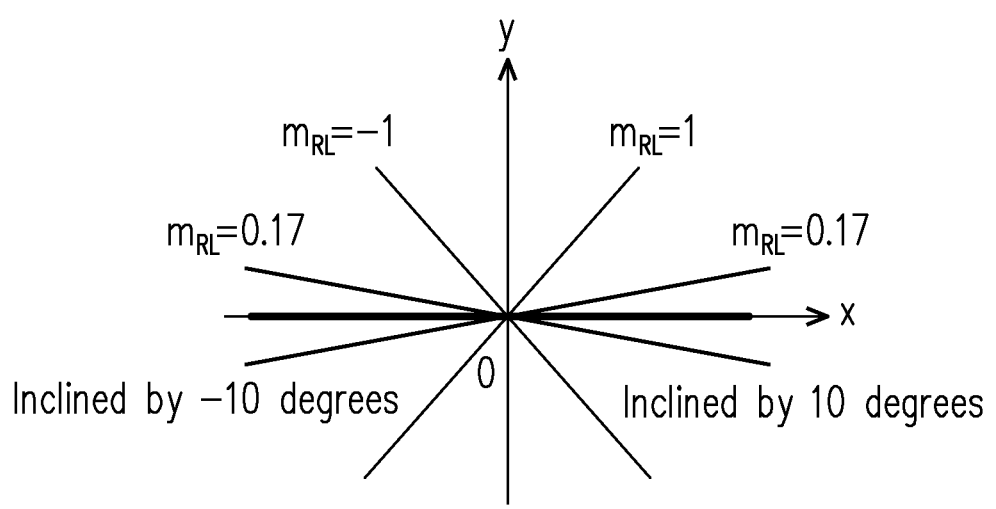

For example, FIG. 4A and FIG. 4B are schematic diagrams illustrating the actions for correcting the operation according to an embodiment of the disclosure. With reference to FIG. 4A, in this embodiment, the gravity sensor is disposed on each of two ends A and B on a handle 42 of a weight training apparatus 40 to detect changes in coordinates of the two ends A and B ($X_R$, $Y_R$) and ($X_L$, $Y_L$) when the user applies the force, calculate a slope $m_{RL}$ based on the two coordinates, compare the slope with the an inclined angle tolerance set by the user or preset by the system, and determine whether the handle 42 is skew. Taking FIG. 4B as an example and assuming that the inclined angle tolerance set by the user is ±10 degrees in a horizontal direction (corresponding to a slope of ±0.17), if the calculated slope $m_{RL}$ is greater than 0.17 or less than −0.17, it can be determined that the handle 42 is skew so that the user is prompted to correct the operation.

On the other hand, the computing device 150 can detect received force of the handle of the weight training apparatus (i.e., positions where the users hold the handle) when the user operates the weight training apparatus by pressure sensors disposed on the two ends of the handle, and determine whether the force applied by the user is balanced according to the detected received force to prompt the user to correct the operation. Similarly, the computing device 150 can compare a difference between the received force with a received force difference tolerance set by the user or preset by the system to determine whether the force applied by the user is balanced, and prompt the user to correct the operation according a determination result.

Returning to the flow in FIG. 3, in step S304, the computing device 150 detects a force applied by each muscle portion when the user operates the weight training apparatus by the biophysical quantity sensor 130, and thereby calculates an energy power consumed by the user. In an embodiment, before the user starts the training, for example, an MVIC (maximum voluntary isometric contraction) of a maximum load (kg) that a muscle of the user can bear is detected first, and then an EMG signal of the muscle may be converted into the applied force F (kg) of the muscle by using the MVIC. Subsequently, the applied force of the muscle is multiplied by the velocity V (m/s) detected by the equipment (e.g., the load) to obtain an energy power consumed by the muscle in the current training.

Then, in step S306, an exercise efficiency value of the user is calculated by using the energy power and the operation power, and the user is prompted to adjust an operation performed on the weight training apparatus or a provider of the weight training apparatus (e.g., the Gym operator) is prompted to eliminate an abnormality when the exercise efficiency value drops beyond a preset ratio. In an embodiment, the computing device 150 uses the ratio of the energy power consumed by the user and the device operation power as the exercise efficiency value, and sets the preset ratio to any value between 30% and 80% (which can be set by the user). Accordingly, during the process of the weight training, whether the exercise efficiency value drops beyond the preset ratio can be continuously monitored. In this way, whether the user encounters the muscle fatigue may be determined so that the user can be prompted to reduce the load or rest in order to prevent the sport injuries.

In an embodiment, the computing device 150 can determine whether the weight training apparatus encounters the abnormality or the operation of the user is inappropriate by determining whether the calculated exercise efficiency value is greater than 1. The abnormality is, for example, a screw looseness or a balance point offset, but not limited thereto. Here, when the exercise efficiency value is greater than 1, a work applied by the muscle is greater than a work received by the load, and thus the computing device 150 can determine that the weight training apparatus encounters the abnormality and prompt the provider (e.g., the Gym operator) of the weight training apparatus to eliminate the abnormality; when the exercise efficiency value is equal to 1, the work applied by the muscle is equal to the work received by the load, and thus the computing device 150 can determine the weight training apparatus is functioning normally; when the exercise efficiency value is less than 1, the work applied by the muscle is less than the work received by the load, and thus the computing device 150 can determine that the operation of the user is inappropriate and prompt the user to adjust the operation (e.g., correct the postures or actions).

Based on the method for calculating the operation power of the weight training apparatus, in an embodiment, the computing device can estimate a most appropriate weight of the user operating the weight training device according to parameter changes in the motion of the load detected when the user operates loads of different weights, and can calculate an appropriate rest time based on a muscle recovery ability detected in advance after the training to thereby improve the weight training effect. The respective embodiments will be described in detail below.

Figure 5:
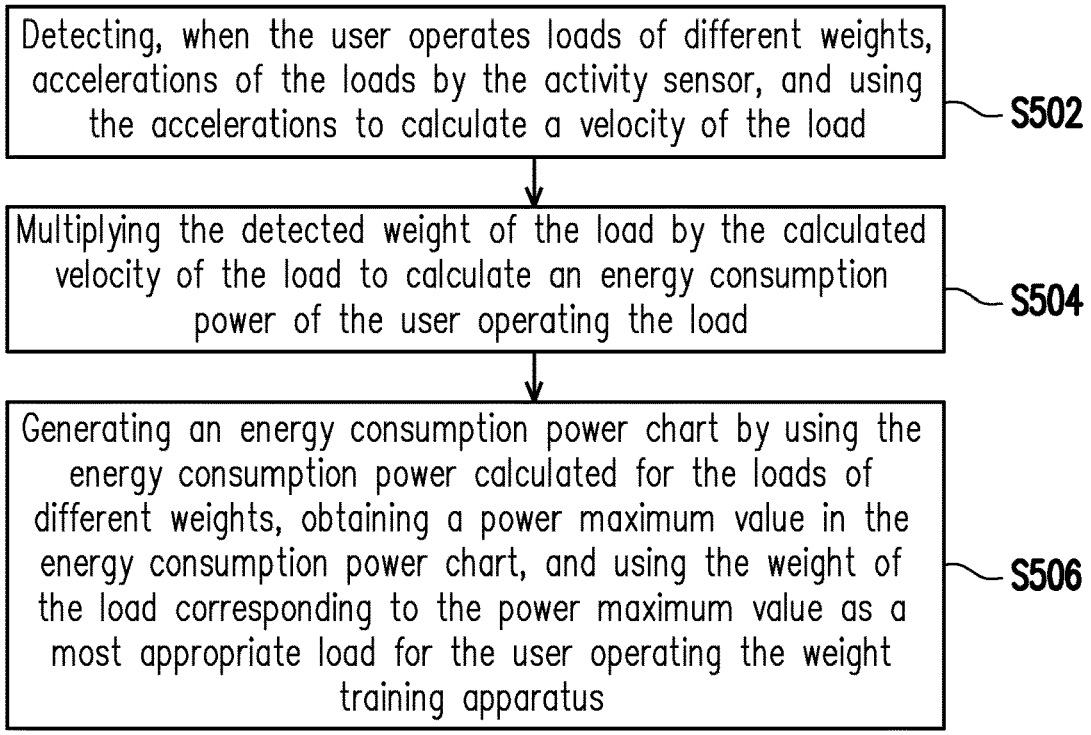
FIG. 5 illustrates a flowchart of a method for calculating a most appropriate load according to an embodiment of the disclosure.

FIG. 5 illustrates a flowchart of a method for calculating a most appropriate load according to an embodiment of the disclosure. Referring to FIG. 1 and FIG. 5 together, the method of this embodiment is adapted to the weight training system 100 of FIG. 1. Detailed steps in the method for calculating the most appropriate weight according to the embodiments of the disclosure are described below with reference to interactions between various devices in the weight training system 100.

First, in step S502, when the user operates loads of different weights, the computing device 150 detects accelerations of the loads by the activity sensor 120, and uses the accelerations to calculate a velocity of the load. Here, the computing device 150 calculates the velocity of the load by, for example, performing the integral operation on the detected accelerations.

In step S504, the computing device 150 uses the weight of the load detected by the load sensor 110 and the velocity of the load calculated from the previous step to calculate an energy consumption power of the user operating the load.

In step S506, the computing device 150 generates an energy consumption power chart by using the energy consumption power calculated for the loads of different weights, obtains a power maximum value in the energy consumption power chart, and uses the weight of the load corresponding to the power maximum value as a most appropriate load for the user operating the weight training apparatus.

Figure 6:
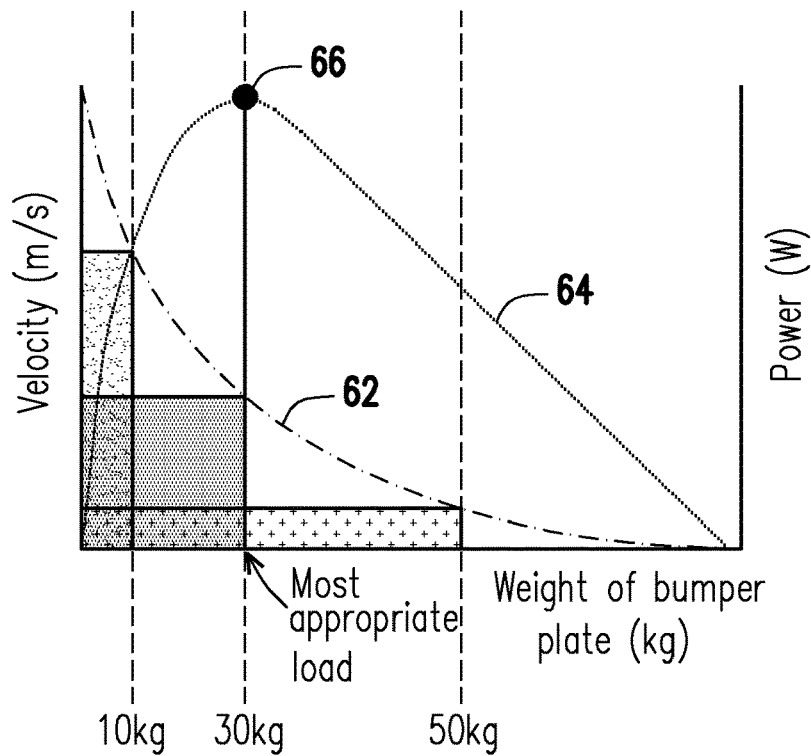
FIG. 6 illustrates an example of the method for calculating the most appropriate load according to an embodiment of the disclosure.

For example, FIG. 6 illustrates an example of the method for calculating the most appropriate load according to an embodiment of the disclosure. With reference to FIG. 6, in this embodiment, for example, in a warm-up phase, by prompting the user to operate bumper plates (the loads) of different weights and detecting the accelerations and the weights of the bumper plates by the sensors disposed on the bumper plates, a relation chart (e.g., a curve 62 in the drawing) of the velocity (m/s) of the bumper plate and the weight (kg) of the bumper plate may be calculated. Here, the applied force F generated by the bumper plate is obtained by multiplying the weight of each bumper plate by the respective velocity. The energy consumption power (W) of the user operating the load is calculated by multiplying the applied force F by the velocity of the bumper plate. Then, an energy consumption power chart (e.g., a curve 64 in the drawing) is generated by using the energy consumption power calculated for the loads of different weights. Accordingly, by obtaining a power maximum value (e.g., a point 66 in the drawing) in the energy consumption power chart, the weight of the load (e.g., 30 kg in the drawing) corresponding to the power maximum value can be used as the most appropriate load for the user operating the weight training apparatus.

Figure 7:
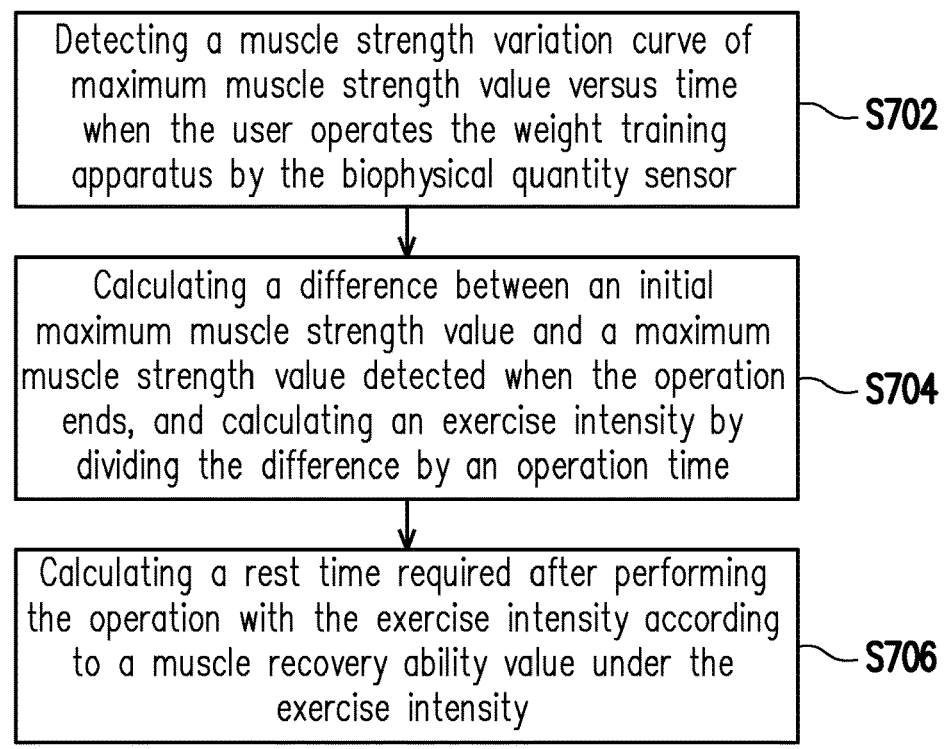
FIG. 7 illustrates a flowchart of a method for calculating a rest time according to an embodiment of the disclosure.

FIG. 7 illustrates a flowchart of a method for calculating a rest time according to an embodiment of the disclosure. Referring to FIG. 1 and FIG. 7 together, the method of this embodiment is adapted to the weight training system 100 of FIG. 1. Detailed steps in the method for calculating the rest time according to the embodiments of the disclosure are described below with reference to interactions between various devices in the weight training system 100.

In step S702, the computing device 150 detects a muscle strength variation curve of maximum muscle strength value versus time when the user operates the weight training apparatus by the biophysical quantity sensor 130. Here, the computing device 150 can prompt the user to attach the biophysical quantity sensor 130 onto the muscle portion to be trained by displaying the prompt screen on the prompt device 140, and can prompt the user to select the most appropriate weight for the weight training by displaying the most appropriate weight calculated from the foregoing embodiment on the prompt device 140.

In step S704, the computing device 150 calculates a difference between an initial maximum muscle strength value and a maximum muscle strength value detected when the operation ends, and calculates an exercise intensity by dividing the difference by an operation time.

In step S706, the computing device 150 calculates a rest time required after performing the operation with the exercise intensity according to a muscle recovery ability value under the exercise intensity.

Figure 8:
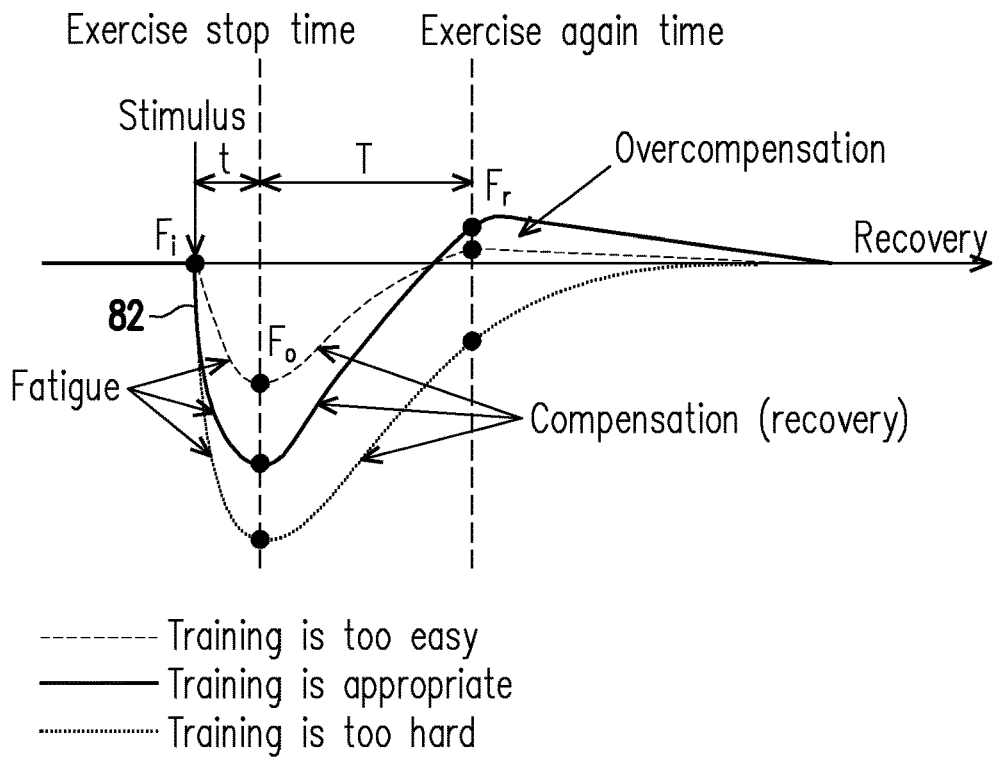
FIG. 8 illustrates an example of the method for calculating the rest times according to an embodiment of the disclosure.

For example, FIG. 8 illustrates an example of the method for calculating the rest times according to an embodiment of the disclosure. With reference to FIG. 8, in this embodiment, for example, the maximum muscle strength value of the muscle portion detected by the biophysical quantity sensor during the training is continuously obtained by the computing device and recorded as a variation curve 82 of maximum muscle strength value versus time. At an exercise stop time, the computing device can calculate an exercise intensity I (the unit is Newton/minute) by subtracting a maximum muscle strength value $F_o$, detected when the operation ends from an initial maximum muscle strength value $F_i$, and then divide the result by an exercise time t:

$$I = \frac{F_i - F_o}{t}$$

Then, the computing device gives advice on the number of rest hours according to the muscle recovery ability detected in advance. In an embodiment, before the user uses the weight training apparatus for the weight training, for example, the computing device can prompt the user to adjust the load, so as to detect the muscle strength variation curve under different exercise intensities, calculate a difference between the maximum muscle strength value $F_o$ when the operation ends and a maximum value $F_r$ of a recovered maximum muscle strength value in the muscle strength variation curve (e.g., $F_r - F_o$), and divide the difference by the operation time T to obtain each of muscle recovery ability values H under the exercise intensities:

$$H = \frac{F_r - F_o}{T}$$

By the above method, the computing device according to the embodiments of the disclosure can calculate the rest time required for recovering the maximum muscle strength to the maximum extent according to the exercise intensity of the user operating the weight training device, and prompt the user to exercise again after a proper rest. Accordingly, the user can obtain a higher weight training effect in a short time.

In summary, during the process of the weight training, the weight training method, the weight training apparatus and the weight training system according to the embodiments of the disclosure can respectively detect the device operation power generated by the work of the device and the energy power consumed by the human muscle that applies the force by the sensors. By analyzing the changes between the two powers, whether there are conditions like inappropriate gestures/actions, inappropriate use of equipment or abnormal equipment during the weight training may be determined. Correspondingly, the user can be prompted to correct gestures or to rest properly, or the gym operator may be prompted to maintain the fitness equipment. In this way, the user can improve the weight training effect and avoid sports injuries.

It will be apparent to those skilled in the art that various modifications and variations can be made to the disclosed embodiments. It is intended that the specification and examples be considered as exemplary only, with a true scope of the disclosure being indicated by the following claims and their equivalents

The invention claimed is:

1. A weight training method, adapted to a weight training system comprising a computing device, a load sensor, an activity sensor and at least one biophysical quantity sensor, the biophysical quantity sensor being disposed on at least one muscle portion of a user, and the method comprising:
   detecting a weight of a load of the user operating a weight training apparatus by the load sensor, detecting a motion of the load by the activity sensor, and thereby calculating an operation power of the weight training apparatus;
   detecting a force applied by the at least one muscle portion when the user operates the weight training apparatus by the biophysical quantity sensor, and thereby calculating an energy power consumed by the user; and
   calculating an exercise efficiency value of the user by using the energy power and the operation power, and prompting the user to adjust an operation performed on the weight training apparatus when the exercise efficiency value drops beyond a preset ratio.

2. The weight training method according to claim 1, further comprising:
   when the user operates loads of different weights, detecting accelerations of the loads by the activity sensor, and using the accelerations to calculate a velocity of the load;
   multiplying the detected weight of the load by the calculated velocity of the load to calculate an energy consumption power of the user operating the load; and
   generating an energy consumption power chart by using the energy consumption power calculated for the loads of different weights, obtaining a power maximum value in the energy consumption power chart, and using the weight of the load corresponding to the power maximum value as a most appropriate load for the user operating the weight training apparatus.

3. The weight training method according to claim 1, further comprising:
   detecting a muscle strength variation curve of maximum muscle strength value versus time when the user operates the weight training apparatus by the biophysical quantity sensor;
   calculating a difference between an initial maximum muscle strength value and a maximum muscle strength value detected when the operation ends, and calculating an exercise intensity by dividing the difference by an operation time; and
   calculating a rest time required after performing the operation with the exercise intensity according to a muscle recovery ability value under the exercise intensity.

4. The weight training method according to claim 3, further comprising:
   calculating a difference between a maximum muscle strength value when the operation ends and a maximum value of the maximum muscle strength value after being recovered in the muscle strength variation curve detected under different exercise intensities, and dividing the difference by the operation time to obtain the muscle recovery ability value under each of the exercise intensities.

5. The weight training method according to claim 1, wherein the step of detecting the force applied by the at least one muscle portion when the user operates the weight training apparatus by the biophysical quantity sensor further comprises:

detecting an inclined angle of a handle of the weight training apparatus when the user operates the weight training apparatus by at least one gravity sensor disposed on the handle; and determining whether the handle is skew according to the detected inclined angle to prompt the user to correct the operation.

6. The weight training method according to claim 1, wherein the step of detecting the force applied by the at least one muscle portion when the user operates the weight training apparatus by the biophysical quantity sensor further comprises:

detecting a received force of a handle of the weight training apparatus when the user operates the weight training apparatus by at least two pressure sensors disposed on two ends of the handle; and determining whether the force applied by the user is balanced according to the detected received force to prompt the user to correct the operation.

7. The weight training method according to claim 1, wherein the step of calculating the exercise efficiency value of the user by using the energy power and the operation power comprises calculating a ratio of the energy power and the operation power as the exercise efficiency value, and the weight training method further comprises:

determining that the weight training apparatus encounters an abnormality when the exercise efficiency value is greater than 1, and prompting a provider of the weight training apparatus to eliminate the abnormality; or determining that the operation of the user is inappropriate when the exercise efficiency value is less than 1, and prompting the user to adjust the operation.

8. A weight training system, comprising:

a load sensor, detecting a weight of a load of a weight training apparatus;

an activity sensor, detecting a motion of the load;

at least one biophysical quantity sensor, disposed on at least one muscle portion of a user, and detecting a force applied by the at least one muscle portion when the user operates the weight training apparatus; and a computing device, coupled to the load sensor, the activity sensor and the biophysical quantity sensor, and configured for:

calculating an operation power of the weight training apparatus by using the detected weight of the load and the detected motion of the load;

using the detected force applied by the at least one muscle portion to calculate an energy power consumed by the user; and calculating an exercise efficiency value of the user by using the energy power and the operation power, and prompting the user to adjust an operation performed on the weight training apparatus when the exercise efficiency value drops beyond a preset ratio.

9. The weight training system according to claim 8, wherein the computing device is further configured for:

when the user operates loads of different weights, detecting accelerations of the loads by the activity sensor, and using the accelerations to calculate a velocity of the load;

multiplying the detected weight of the load by the calculated velocity of the load to calculate an energy consumption power of the user operating the load; and generating an energy consumption power chart by using the energy consumption power calculated for the loads of different weights, obtaining a power maximum value in the energy consumption power chart, and using the weight of the load corresponding to the power maximum value as a most appropriate load for the user operating the weight training apparatus.

10. The weight training system according to claim 8, wherein the computing device is further configured for:

detecting a muscle strength variation curve of maximum muscle strength value versus time when the user operates the weight training apparatus by the biophysical quantity sensor;

calculating a difference between an initial maximum muscle strength value and a maximum muscle strength value detected when the operation ends, and calculating an exercise intensity by dividing the difference by an operation time; and calculating a rest time required after performing the operation with the exercise intensity according to a muscle recovery ability value under the exercise intensity.

11. The weight training system according to claim 10, wherein the computing device is further configured for:

calculating a difference between a maximum muscle strength value when the operation ends and a maximum value of the maximum muscle strength value after being recovered in the muscle strength variation curve detected under different exercise intensities, and dividing the difference by the operation time to obtain the muscle recovery ability value under each of the exercise intensities.

12. The weight training system according to claim 8, further comprising:

at least one gravity sensor, disposed on a handle of the weight training apparatus, and detecting an inclined angle of the handle when the user operates the weight training apparatus, wherein the computing device further determines whether the handle is skew according to the detected inclined angle to prompt the user to correct the operation.

13. The weight training system according to claim 8, further comprising:

at least two pressure sensors, disposed on two ends of a handle of the weight training apparatus, and detecting a received force of the handle when the user operates the weight training apparatus, wherein the computing device further determines whether the force applied by the user is balanced according to the detected received force to prompt the user to correct the operation.

14. The weight training system according to claim 8, wherein the computing device is further configured for:

determining that the weight training apparatus encounters an abnormality when the exercise efficiency value is greater than 1, and prompting a provider of the weight training apparatus to eliminate the abnormality; or determining that the operation of the user is inappropriate when the exercise efficiency value is less than 1, and prompting the user to adjust the operation.

15. A weight training system, comprising:

a load sensor, detecting a weight of a load of a weight training apparatus;

an activity sensor, detecting a motion of the load;

at least one biophysical quantity sensor, disposed on at least one muscle portion of a user, and detecting a force applied by the at least one muscle portion when the user operates the weight training apparatus; and a computing device, coupled to the load sensor, the activity sensor and the biophysical quantity sensor, and configured for:

calculating an operation power of the weight training apparatus by using the detected weight of the load and the detected motion of the load;

using the detected force applied by the at least one muscle portion to calculate an energy power consumed by the user; and calculating an exercise efficiency value of the user by using the energy power and the operation power, wherein the weight training apparatus is determined as being encountering an abnormality when the exercise efficiency value is greater than 1, and a provider of the weight training apparatus is prompted to eliminate the abnormality; or the operation of the user is determined as being inappropriate when the exercise efficiency value is less than 1, and the user is prompted to adjust the operation.

\* \* \* \* \*